United States Patent [19]

Klas et al.

[11] Patent Number: 4,699,010

[45] Date of Patent: Oct. 13, 1987

[54] HIGH-TEMPERATURE RESISTANT ELONGATION MEASURING SYSTEM FORMED OF CERAMIC MATERIALS

[75] Inventors: Ernst Klas, Lohmar; Rudolf Schmidt, Rösrath; Günther Schumacher, Alsdorf; Dieter Stausebach, Bergisch Gladbach; Alfred Zentis, Eschweiler, all of Fed. Rep. of Germany

[73] Assignee: Interatom GmbH, Bergisch Gladbach, Fed. Rep. of Germany

[21] Appl. No.: 871,701

[22] Filed: Jun. 6, 1986

[30] Foreign Application Priority Data

Jun. 10, 1985 [DE] Fed. Rep. of Germany ....... 3520770

[51] Int. Cl.$^4$ .............................................. G01B 7/18
[52] U.S. Cl. ................................................... 73/774
[58] Field of Search ...................... 73/862.65, 763, 774; 338/2, 3, 4; 29/610 SG

[56] References Cited

U.S. PATENT DOCUMENTS

| 2,481,371 | 9/1949 | Van Dyke | 29/610 SG X |
| 3,197,335 | 7/1965 | Leszynski | 338/2 X |
| 3,429,020 | 2/1969 | Russell | |
| 4,197,753 | 4/1980 | Harting et al. | 73/766 |

FOREIGN PATENT DOCUMENTS

| 0532592 | 2/1982 | Australia. |
| 0088278 | 7/1984 | European Pat. Off.. |
| 0137565 | 4/1985 | European Pat. Off.. |
| 2501362 | 3/1981 | France. |
| 1470591 | 4/1977 | United Kingdom. |
| 2068562 | 8/1981 | United Kingdom. |
| 2083012 | 3/1982 | United Kingdom. |

Primary Examiner—Jerry W. Myracle
Attorney, Agent, or Firm—Herbert L. Lerner; Laurence A. Greenberg

[57] ABSTRACT

A device for measuring elongation of a structure includes mounts formed at least partially of electrically insulating ceramic material, the mounts having at least two points to be attached to a structure for shifting the mounts relative to each other upon elongation of the structure, and electrically conducting parts disposed on the mounts having electrical properties being influenced by the shifting of the mounts, at least a portion of each of the electrically conducting parts being subjected to mechanical stresses, and at least the portions of the electrically conducting parts being formed of electrically conductive ceramic material.

19 Claims, 13 Drawing Figures

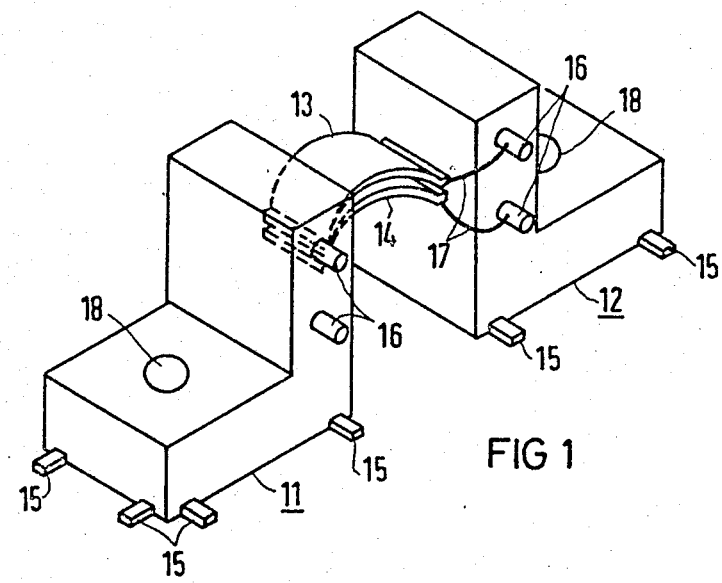
FIG 1
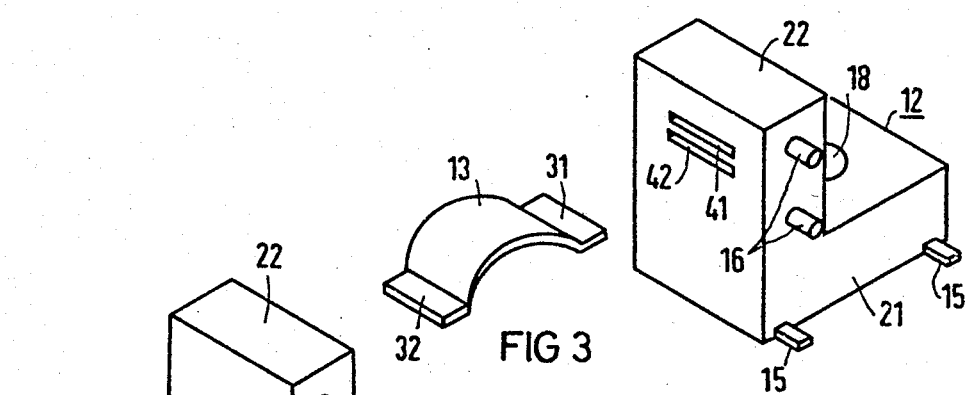
FIG 3
FIG 4
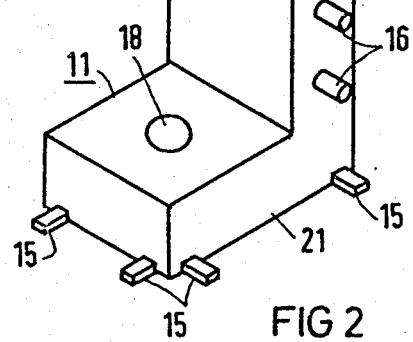
FIG 2

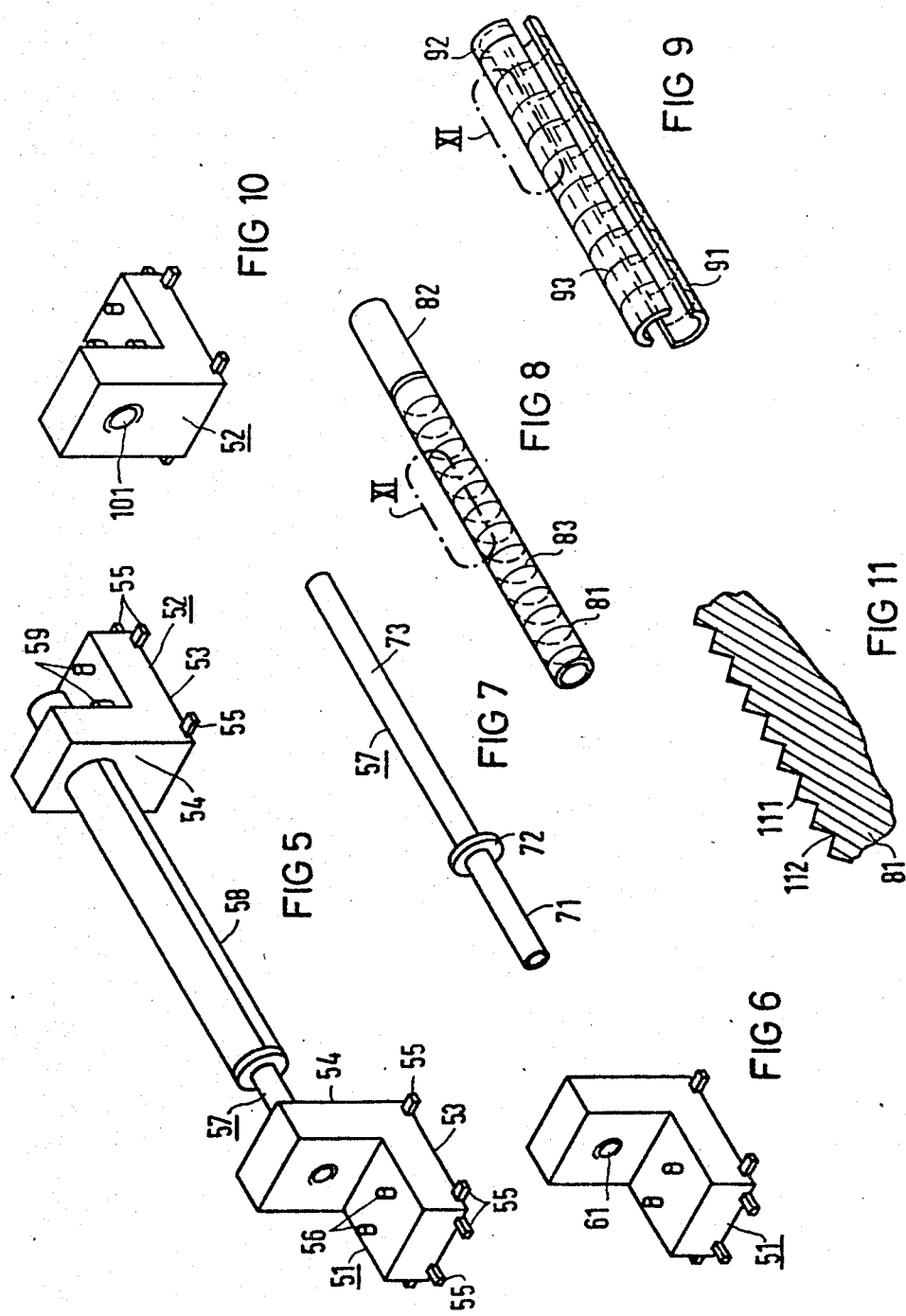

HIGH-TEMPERATURE RESISTANT ELONGATION MEASURING SYSTEM FORMED OF CERAMIC MATERIALS

The invention relates to a high-temperature resistant elongation measuring system formed of ceramic material, including mounts to be attached to a structure at least at two points for shifting the mounts relative to each other upon elongation of the structure, the mounts being provided with, electrically conducting parts having electrical properties being influenced by the shift.

In many fields of technology, smaller and larger length changes, such as those due to material expansion, must be measured as precisely as possible. Many different elongation measuring systems are known for low and medium temperature ranges up to several hundred degrees Celsius.

For instance, British patent No. 1,470,591 describes a capacitive elongation measuring pickup. Inductive distance pickups and so-called wire strain gauges with conductors wound in meander fashion are also within the state of the art.

Finally, elongation measuring pickups for higher temperature ranges are also known, such as are described in European patent No. 0 088 278. However, no suitable measuring pickups have been proposed to date for temperatures in which metals can no longer be used as the electrically conducting parts which are simultaneously mechanically stressed.

It is accordingly an object of the invention to provide a hightemperature resistant elongation measuring system formed of ceramic materials, which overcomes the hereinafore-mentioned disadvantages of the heretofore-known devices of this general type, and which is suited for temperature ranges in which metals can no longer be used as mechanically stable structural parts. In particular, temperature ranges above 900° C. or even 1000° C. should be given consideration. Conventional measurement principles and devices are to be used by applying suitable measures.

With the foregoing and other objects in view there is provided, in accordance with the invention, a device for measuring elongation of a structure, comprising mounts formed at least partially of electrically insulating ceramic material, the mounts having at least two points to be attached to a structure for shifting the mounts relative to each other upon elongation of the structure, and electrically conducting parts or structural members disposed on the mounts having electrical properties or characteristics being influenced by the shifting of the mounts, at least a portion of each of the electrically conducting parts being subjected to mechanical stresses, and at least the portions of the electrically conducting parts being formed of electrically conductive material, or as far as they are subjected to mechanical stress, strain or load.

In accordance with another feature of the invention, the mounts are formed of aluminum oxide ($Al_2O_3$).

In accordance with a further feature of the invention, portions of the mounts are also formed of electrically conductive ceramic materials.

In accordance with an added feature of the invention, the electrically conductive ceramic material is carbon reinforced with carbon fibers (CFC).

The decisive step according to the invention is the transition from metallic materials to ceramic materials which nevertheless have suitable electric conductivity. In recent years, for instance, the development of carbon fiber-reinforced carbon, which will be referred to as CFC below, has greatly advanced. CFC has become an easily handled flexible material of high strength in the high temperature region. This material, which was developed initially for use in large parts such as pipelines and supporting structures, is surprisingly suited for very small parts as well and can be employed there in place of the metals used heretofore, even in the range of the highest temperatures. Other conductive ceramics which have been developed are also suited for solving such problems. Through the use of electrically insulating ceramic mounts for the CFC parts, measuring devices according to known measurement principles can be constructed without using metallic material.

In accordance with an additional feature of the invention, the mounts have metallic pins at the points for fastening the mounts to the structure and pins for fastening electrical leads to the mounts. When making measurements on metallic structures, it is often advantageous to fasten the measuring pickups by such metallic pins. The leads also require fastening points for load-relief and for connection to the sensitive parts of the measuring device itself.

As an alternative thereto, in accordance with again another feature of the invention, the mounts have slightly conically narrowed holes formed therein leading toward the structure for receiving ceramic fastening bolts.

In accordance with again a further feature of the invention, the electrically conducting parts are formed of oxidation-resistant ceramic material such as CFC coated with silicon carbide or carbon (SiC). This is used for applications in which there is no inert ambient atmosphere. In some circumstances, covering with a tight cap is sufficient without further measures, where the oxygen within the cap is not sufficient to substantially damage the CFC. However, if desired the interior of the cap can also be rendered inert.

In accordance with again an added feature of the invention, the electrically conducting parts form a capacitor having a capacity dependent on the spacing between the mounts. This measuring principle and the basic structure of such a measuring transducer are known, but the peculiarities of the new materials must be taken into consideration.

Accordingly, in accordance with again an additional feature of the invention, the electricaly conducting parts are two substantially mutually parallel bent electrically conducting ceramic plates preferably formed of CFC each having two sides fastened in openings formed in the mounts closely fitting the sides.

In contrast to the state of the art, separate capacitor plates are not fastened to an elastic bracket, but brackets themselves simultaneously form the capacitor plates as well. While this requires preparation of a calibration curve of the capacity as a function of the spacing between the mounts, it simplifies the construction of the pickup and reduces the number of required parts.

In accordance with still another feature of the invention, the electrically conducting parts include a detunable coil system with coils having an insulation dependent on the spacing between the mounts so as to form an elongation or travel distance pickup In this case as well, the use of new materials opens up higher temperature ranges.

In accordance with still a further feature of the invention, the coil system is fastened to one of the mounts, and including an electrically conducting rod preferably formed of CFC being fastened to the other of the mounts and extended into the coil system by a distance being shifted in dependence on the spacing between the mounts.

In accordance with still an added feature of the invention, the coil system is screwed into the one mount and the rod is screwed into the other mount.

In accordance with still an additional feature of the invention, the coil system includes a transmitting coil and a receiving coil having a mutual induction being influenced by the rod.

In accordance with yet another feature if the invention, the coil system includes a core on which the coils are wound in the shape of a double-thread screw.

In accordance with yet a further feature of the invention, the coil system includes a core on which one of the coils is wound and an insulating layer disposed on the core on which the other of the coils is wound.

The new materials are also suited for use in a device applying the principle of a free-grid strain gauge. In accordance with yet an added feature of the invention, the electrically conducting parts form a free-grid wire strain gauge having electrically conducting fibers formed of CFC or pure graphite. In such a device, the metallic conductors disposed in meander shape, which are used according to the state of the art, are replaced by electrically conducting fibers of CFC or pure graphite. The shape of the lateral mounts is adapted correspondingly.

In accordance with a concomitant feature of the invention, the electrically conducting parts form a free-grid wire strain gauge formed of carbon filaments wound in meander form and subsequently coked.

Other features which are considered as characteristic for the invention are set forth in the appended claims.

Although the invention is illustrated and described herein as a high-temperature resistant elongation measuring system formed of ceramic materials, it is nevertheless not intended to be limited to the details shown, since various modifications and structural changes may be made therein without departing from the spirit of the invention and within the cope and range of equivalents of the claims.

The construction and method of operation of the invention, however, together with additional objects and advantages thereof will be best understood from the following description of specific embodiments when read in connection with the accompanying drawings, in which:

FIG. 1 is a diagrammatic, perspective view of a capacitive elongation measuring pickup according to the invention;

FIGS. 2, 3 and 4 are perspective views of the parts of the pickup of FIG. 1

FIG. 5 is a perspective view of an inductive distance pickup;

FIGS. 6, 7, 8, 9 and 10 are perspective views of parts of the distance pickup of FIG. 5;

FIG. 11 is an enlarged, fragmentary, cross-sectional view of the portion XI in FIG. 8;

Figure 12:
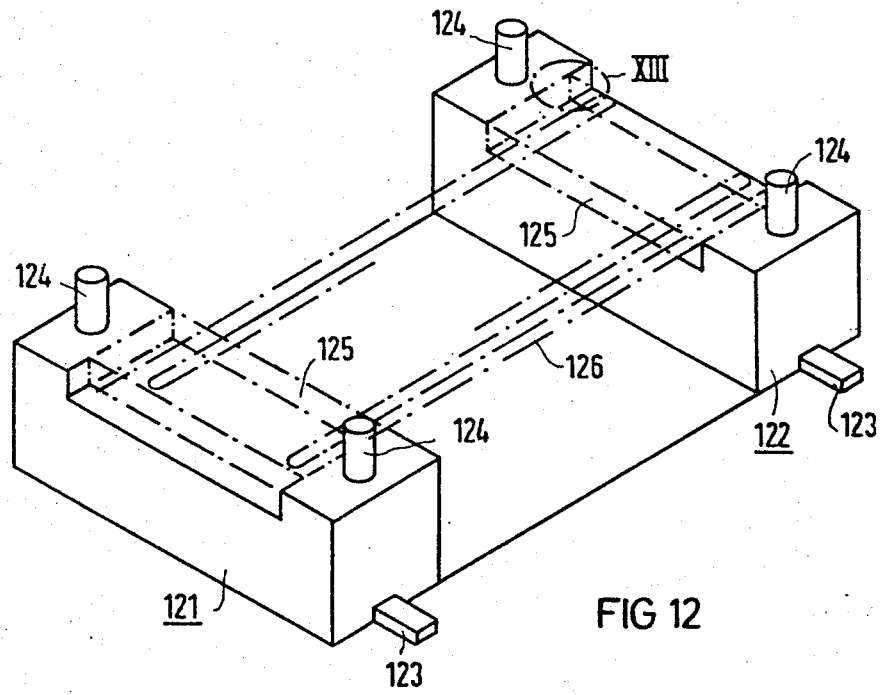
FIG. 12 is a perspective view of a free grid elongation measuring pickup.

Referring now to the figures of the drawings in detail and first, particularly, to FIG. 1 thereof, there is seen an overall view of a capacitive elongation measuring pickup for high temperatures according to the invention. The pickup is formed of two angular mounts 11, 12 which may be identical or may be mirror-symmetrical, and two bent strips 13, 14 of electrically conductive ceramic material, preferably CFC, forming the capacitor. The individual parts are also shown in detail in FIGS. 2, 3 and 4. Each of the mounts 11, 12 has metallic pins 15 which are worked into the ceramic material on the side thereof intended for contact in order to permit fastening to a structure, such as by spot welding. In addition, or as an alternative thereto, holes 18 which are slightly conically narrowed downward, are provided in the legs of the mounts 11, 12 to be placed on the structure, in order to permit fastening by ceramic bolts or the like. Furthermore, fastening pins 16 are worked into the legs of the mounts 11, 12 which carry the capacitor strips or plates. The pins 16 serve as fastening points for electrical leads and for stress relief of the electrical leads. The capacitor plates 13, 14 proper are of identical construction and can be inserted into closely fitting openings 41, 42 in the mounts 11, 12. To this end, the capacitor plates 13, 14 each have suitably formed sections 31, 32 at both ends thereof Electrically conducting connections 17 lead from each capacitor plate 13, 14 to the fastening pins 16. If CFC is used for the capacitor plates, some of the carbon fibers used therein can simply protrude and be used as the leads 17.

In FIGS. 5 to 11, an inductive distance measuring pickup is shown with its individual parts. The explanation given above regarding the fastening of mounts on a structure also apply to angular mounts 51, 52 shown in FIGS. 5-11. The mounts 51, 52 can be fastened in such a way that their legs 53 rest on the structure. This is accomplished by means of metallic pins 55 inserted into the ceramic material, or by means of ceramic bolts passing through suitable non-illustrated holes, as explained above. The function of fastening pins 56, 59 also remains unchanged in principle. The inductive distance measuring pickup is formed of a coil system assembly 58 which is fastened to the mount 52 and an electrically conducting rod 57, which is preferably made of CFC and is fastened to the other mount 51. The rod shifts in the interior of the coil system if the spacing between the mounts 51, 52 changes. This shift changes the induction of the coil system; the change can be measured and serves as a measurement of the shift. In the illustrated embodiment, the electrically conducting rod 57 which can be shifted in the interior of the coil system 58, is constructed in three sections. A threaded section 71 can be screwed into a corresponding mating thread 61 in one leg 54 of the mount 51. A stop 72 limits the depth of penetration of an electrically conducting section 73 which serves for detuning the coil system 58. The coil system itself is formed of a support tube or cone 81 and at least one coil 83 wound thereon. The coil is preferably wound into troughs or valleys 112 of an appropriately formed helix 111 of the support tube 81. A threaded section 82 of the support tube 81 can be screwed in a corresponding mating thread 101 in one leg of the mount 52. Frequently, the detuning of only one coil cannot be measured with sufficient measuring accuracy. The coil system is therefore preferably constructed of two coils, one of which serves as a transmitter coil and the other as a receiver coil. The two coils can either be wound on the support tube 81 in the form of a two-threaded helix, or they can be disposed concentrically and separated by an insulating layer 91, 92 as indicated in FIG. 9. The insulating layer 91, 92 may be formed of two ceramic half shells which are held together by winding a coil 93 thereon. Optionally, other mounts such as clamps or the like can also be provided. The coils proper may be formed of metallic conductors since they are not stressed mechanically. However, it is also possible to use carbon fibers.

Figure 13:
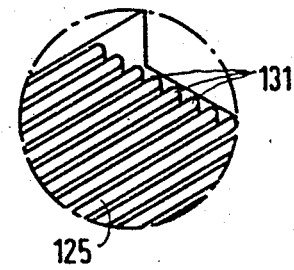
FIG. 13 is an enlarged view of the portion XIII of FIG. 12.

FIGS. 12 and 13 show a further embodiment of the invention. In the FIGS. 12 and 13 device, the conventional principle of the free-grid wire strain gauge is modified for the use of new materials. Mounts 121, 122 have inserted pins 123, 124 which fulfill the same function as the corresponding parts in the embodiment described above. Provisions for fastening the mounts 121, 122 are also made accordingly. In the illustrated embodiment, the mounts 121, 122 have a frame 125 on the side thereof facing away from the structure, around which a carbon filament 126 may be wound in meander fashion. The frame 125 is preferably constructed in the form of a comb and the carbon filament 126 can be placed about rounded tines 131 thereof without damage. The ends of the carbon filament are attached to two fastening pins 124. If the mounts 121, 122 shift relative to each other, the resistance or the inductance of the respective carbon filament changes and this change can be measured. For applications in which the measuring system is not subjected to strong external influences, it is possible to wind a carbon filament in meander fashion and to convert it to coke so that it remains dimensionally stable. In this case, the mounts can be made in a very simple form and need only be suited for fastening the ends of the carbon filament and the leads.

The measuring pickups described above are only examples of the various possible applications of the invention. It is possible to use other ceramic materials with comparable or better properties, especially with respect to oxidation resistance and for some applications, this is necessary. The measuring pickups are suitable for temperatures at which metallic materials under mechanical stress can no longer be used.

We claim:

1. Device for measuring elongation of a structure, comprising mounts formed at least partially of electrically insulating ceramic material, said mounts having at least two points, to be attached to a structure for shifting said mounts relative to each other upon elongation of the structure, and electrically conducting parts disposed on said mounts having electrical properties being influenced by the shifting of said mounts, at least a portion of each of said electrically conducting parts being subjected to mechanical stresses, and at least said portions of said electrically conducting parts being formed of electrically conductive ceramic material.

2. Device according to claim 1, wherein said mounts are formed of aluminum oxide.

3. Device according to claim 1, wherein portions of said mounts are also formed of electrically conductive ceramic material.

4. Device according to claim 3, wherein said electrically conductive ceramic material is carbon reinforced with carbon fibers.

5. Device according to claim 1, wherein said electrically conductive ceramic material is carbon reinforced with carbon fibers.

6. Device according to claim 1, wherein said mounts have metallic pins at said points for fastening said mounts to the structure and pins for fastening electrical leads to said mounts.

7. Device according to claim 1, wherein said mounts have slightly conically narrowed holes formed therein leading toward the structure for receiving ceramic fastening bolts.

8. Device according to claim 1, wherein said electrically conducting parts are formed of oxidation-resistant ceramic material coated with silicon carbide.

9. Device according to claim 1, wherein said electrically conducting parts form a capacitor having a capacity dependent on the spacing between said mounts.

10. Device according to claim 9, wherein said electrically conducting parts are two substantially mutually parallel bent ceramic plates each having two sides fastened in openings formed in said mounts closely fitting said sides.

11. Device according to claim 1, wherein said electrically conducting parts include a detunable coil system with coils having an insulation dependent on the spacing between said mounts.

12. Device according to claim 11, wherein said coil system is fastened to one of said mounts, and including an electrically conducting rod being fastened to the other of said mounts and extended into said coil system by a distance being shifted in dependence on the spacing between said mounts.

13. Device according to claim 12, wherein said coil system is screwed into said one mount and said rod is screwed into said other mount.

14. Device according to claim 12, wherein said coil system includes a transmitting coil and a receiving coil having a mutual induction being influenced by said rod.

15. Device according to claim 14, wherein said coil system includes a core on which said coils are wound in the shape of a double-thread screw.

16. Device according to claim 14, wherein said coil system includes a core on which one of said coils is wound and an insulating layer disposed on said core on which the other of said coils is wound.

17. Device according to claim 1, wherein said electrically conducting parts form a free-grid wire strain gauge having electrically conducting fibers formed of CFC.

18. Device according to claim 1, wherein said electrically conducting parts form a free-grid wire strain gauge having electrically conducting fibers formed of pure graphite.

19. Device according to claim 1, wherein said electrically conducting parts form a free-grid wire strain gauge formed of carbon filaments wound in meander form and subsequently coked.

* * * * *